(12) United States Patent
Wijay (10) Patent No.: US 9,724,101 B2
(45) Date of Patent: Aug. 8, 2017

(54) LUMEN OCCLUDING DEVICE, DELIVERY CATHETER AND METHOD

(71) Applicant: Bandula Wijay, Friendswood, TX (US)

(72) Inventor: Bandula Wijay, Friendswood, TX (US)

(*) Notice: Subject to any disclaimer, the term of this patent is extended or adjusted under 35 U.S.C. 154(b) by 403 days.

(21) Appl. No.: 14/161,415

(22) Filed: Jan. 22, 2014

(65) Prior Publication Data
US 2015/0201945 A1    Jul. 23, 2015

(51) Int. Cl.
*A61B 17/12* (2006.01)
*A61F 6/22* (2006.01)
*A61B 17/00* (2006.01)

(52) U.S. Cl.
CPC .. *A61B 17/12031* (2013.01); *A61B 17/12109* (2013.01); *A61B 17/12113* (2013.01); *A61B 17/12172* (2013.01); *A61F 6/225* (2013.01); *A61B 17/12177* (2013.01); *A61B 2017/00986* (2013.01); *A61B 2017/12054* (2013.01)

(58) Field of Classification Search
CPC ......... A61M 27/008; A61F 6/22; A61F 6/225; A61B 17/12136; A61B 2017/12095; A61B 17/12118
See application file for complete search history.

(56) References Cited

U.S. PATENT DOCUMENTS

| | | | | |
|---|---|---|---|---|
| 6,652,556 B1* | 11/2003 | VanTassel | ........ | A61B 17/12122 606/200 |
| 8,801,746 B1* | 8/2014 | Kreidler | .................... | A61F 2/01 606/200 |
| 2002/0143349 A1* | 10/2002 | Gifford, III | ...... | A61B 17/12022 606/157 |
| 2005/0277983 A1* | 12/2005 | Saadat | ............... | A61B 17/0401 606/215 |
| 2009/0287291 A1* | 11/2009 | Becking | ........... | A61B 17/12022 623/1.11 |
| 2013/0138138 A1* | 5/2013 | Clark | ............... | A61B 17/12022 606/200 |

* cited by examiner

*Primary Examiner* — Thomas McEvoy
(74) *Attorney, Agent, or Firm* — Steve Rosenblatt (57) ABSTRACT

An occlusion device has spaced struts connected by end members and is covered with a sheath. An actuator runs through the frame defined by the struts and end members. The struts are delivered in tension and allowed to relax to flex outwardly for fixation. The struts can also be placed in a relaxed condition and then flexed with relative movement of the end members when coming closer together. The set position of the struts is locked. The actuator can be at least in part removed after the struts flex. An anchor can be placed proximally to the frame and it contains spaced elongated members connected into a tubular shape with circumferential bands that have bends for flexibility to collapse for insertion and expand when placed in the lumen.

20 Claims, 8 Drawing Sheets

LUMEN OCCLUDING DEVICE, DELIVERY CATHETER AND METHOD

FIELD OF THE INVENTION

The present invention relates to an endo-luminal occluding device, which when implanted within a body lumen, such as arteries, veins, fallopian tubes, facilitates immediate occlusion of the lumen. By this means blood supply to tumors, necrotic tissues, and aneurisms can be cut off immediately and help in healing of the affected areas of interest. Similarly an immediate blocking of the fallopian tubes will prevent sperm migration preventing the fertilization of the ovum and hence will provide means of immediate female sterilization.

BACKGROUND OF THE INVENTION

The present invention deals with a method and device that will occlude the body lumen immediately and does not depend of tissue growth to cause the occlusion of the body lumen. Occlusion of body lumens for various medical procedures as well as for female sterilization is a very common practice and is performed frequently throughout the world except in most cases the procedure depends of tissue growth due to the tissue injury to affect closure, which takes time. Often additional tests are conducted at a later date, with additional expenditure, to assure, a closed lumen. Cutting blood supply to tumors is often used to shrink the tumor and similarly cutting blood supply can also alleviate neuropathic pain in the clinical practice. For female sterilization, various devices have been developed in the past and these methods depend on tissue growth within the lumen caused by injury and/or irritation of the fallopian tube tissue by an implanted device for its closure. Additionally, the most common female sterilization method is fallopian tube ligation, a procedure that utilizes a trans-abdominal approach for the occlusion, or tying, of the fallopian tubes, which is surgical, and expensive. Despite its worldwide use, tubal ligation via the trans-abdominal approach is associated with substantial trauma, discomfort, hospital stays, and complications, such as bleeding, infection, reactions to general anesthetic, and bowel perforation. The trans-abdominal approach involves surgery, and is not readily available to many women throughout the world. Even though local anesthetic is considered an option for the trans-abdominal approach to tubal ligation, almost all of these sterilization procedures are performed under general or spinal anesthesia. In addition, the trans-abdominal approach to tubal ligation requires incisions that invade the peritoneal cavity, thereby raising the risk of injury to intra-abdominal structures.

In order to avoid the problems associated with trans-abdominal tubal ligation procedures, various trans-cervical approaches to tubal sterilization have been proposed. The trans-cervical approach to sterilization involves the insertion of a catheter or sterilization device directly into the fallopian tubes via the reproductive tract, eliminating the need for general anesthetic and abdominal incisions. Initial trans-cervical approaches to tubal sterilization involved radiofrequency, chemical or heat induced scarring, or liquid silicone injections. However, these approaches have all failed due to safety and efficacy concerns. Chemical scarring agents, such as quinacrine, iodine, and methylcyanoacrylate, require repeated applications and have problems concerning biocompatibility. Thermal blocking procedures, which induce the formation of scar tissue within the fallopian tubes, have high failure rates and major complications such as uterine bleeding and bowel perforation. Electrocautery methods, which employ an electric current to induce scar tissue within the fallopian tubes, are also unsatisfactory because they do nor scar a sufficient amount of tissue and because they can burn surrounding organs, particularly the bowel.

Current trans-cervical methods involve occluding the fallopian tubes by implanting a small occluding device. The occluding devices in the prior art are usually in the form of a cylindrical plug or a coil. For instance, Loy in U.S. Pat. No. 6,357,443 describes a removable fallopian tube plug consisting of a tubular (cylindrical) elongate member with a number of fingerlike protrusions that extend radially outwards creating a barrier and thereby occluding the fallopian tubes. Additionally, Saadat et al. in U.S. Pat. No. 5,935,137 describe a fallopian tube occluding device for female sterilization which is a plastic, rubber, or metal elongate hollow tubular (cylindrical) structure with ribs that are either coated with copper or are interlaced with copper rings. The hollow portion of this device has a valve, or seals with a hydrogel, after the device is implanted into the fallopian tubes.

Coils, which have a helical outer surface and which assume a bent shape when released from the delivery catheter system, are also used to occlude the fallopian tubes. For example, Ton et al. in U.S. Pat. Nos. 5,601,600 and 5,746,769 describe the use of a coil to occlude the fallopian tubes. The device consists of polyethylene terephthalate (PET) fibers wrapped around a stainless steel core that is surrounded by 24 or more coils of nickel-titanium alloy. After the device is deployed within the fallopian tubes, the PET fibers induce the tubal epithelium to undergo fibrosis, which results in tubal occlusion. The device also relaxes to its natural bent shape once it is deployed in the fallopian tube. The tubal occlusion process from these devices takes about three months to complete and must be confirmed via a hysterosalpingogram.

Figure 3:
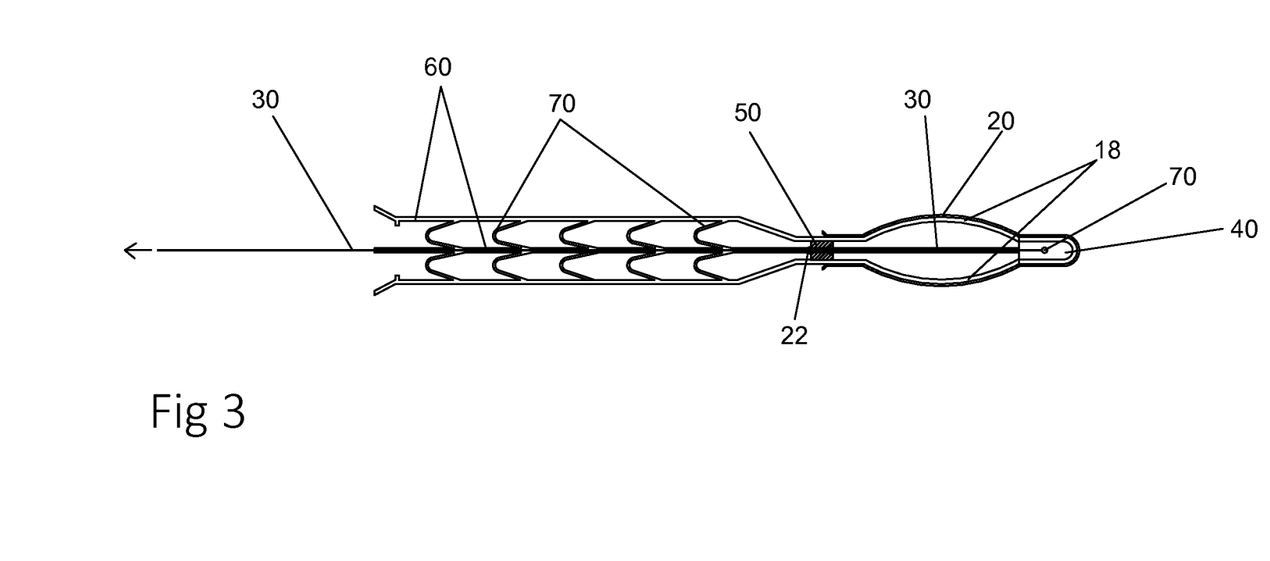
FIG. 3 shows the preferred embodiment in its deployed configuration, the configuration attained once the device has been placed and deployed in a desired body lumen.
Figure 4:
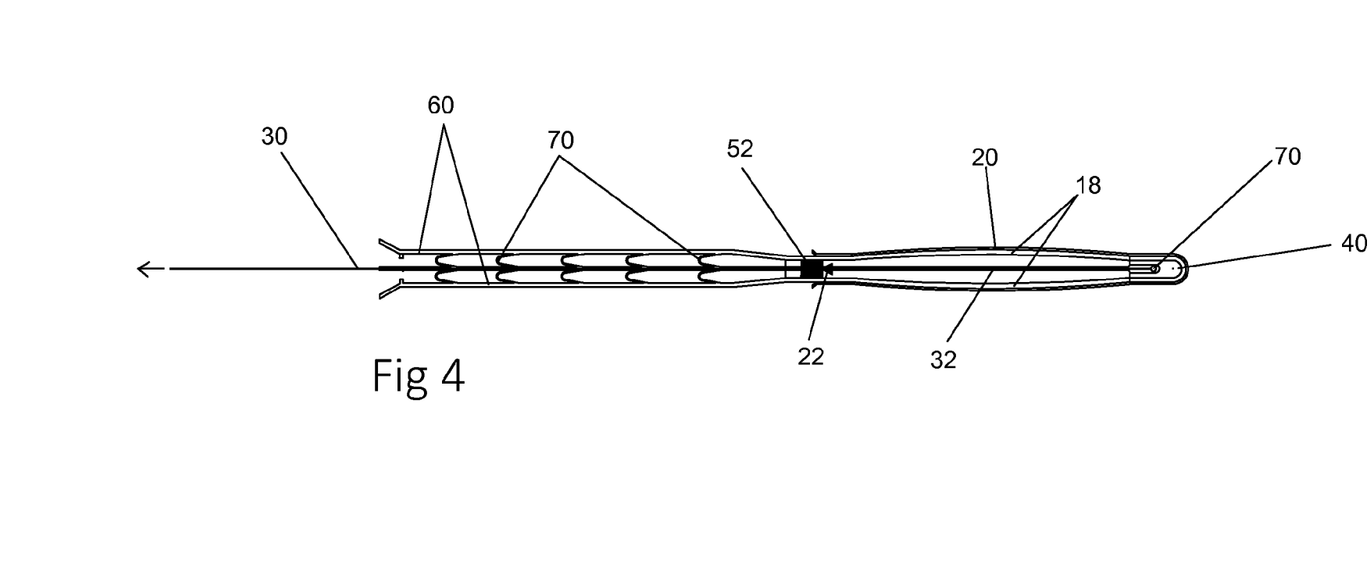
FIG. 4 shows an alternate mechanical actuating means to deliver the occluder into the desired body lumen.

U.S. Pat. No. 7,846,160 teaches the use of an exterior screw thread to advance a lumen plug by rotation In FIG. 3. In FIG. 4 barbs are held under a sheath such that when the sheath is retracted, the barbs spring out and point proximally to prevent removal.

Most of these devices eventually become dislodged or have found to be only moderately effective in preventing pregnancy. In addition, all of the fallopian tube occluding devices are either composed of metal or have metal components. As a result, various surgical procedures involving electrosurgery, radiofrequency, or microwave energy cannot be performed near the implants. Therefore, a need exists for a female contraceptive device that does not contain any metal, does not migrate once implanted, and which provides immediate protection against conception. The occlusion device of the present invention fulfills these needs.

SUMMARY OF THE INVENTION

The present invention consists of a permanent acute implantable occlusion device, or the herein after called the "occluder", and method for immediate occlusion of a body lumen, such as the blood vessels, aneurisms, or the fallopian tubes of the human female. The implant, an acute occlusion device, consists of a small narrow low profile rounded frame and which has a smooth hemi-spherical distal end, which is a continuation of the longitudinal members of a slotted tube, the hemi-spherical end cap is located at the distal end of the said small narrow rounded frame. The longitudinal members of slotted tube frame are at least in part encased in an expandable sheath. The sheath can function as a wall or an occlusion means for a body lumen when it is expanded using an actuator to pull the distal end structure of the rounded frame towards its proximal end structure, or released into a pre-set form by releasing the force holding it in its' low profile stretched form, whereby the rounded frame is transformed from its long narrow low profile shape into an expanded bulbous shape, large enough to completely occlude the body lumen which is to be occluded.

The occlusion means described in the present invention is permanently placed inside a body lumen for occlusion of a body lumen. The occluder is delivered using a delivery catheter device to which the occluder is mounted at its distal end and delivery catheter having releasable means to release the occluder after bringing its distal end structure towards the proximal end structure causing its shape to become a bulbous shape, having a larger profile than its initial profile. Alternatively the occluder may have a bulbous preset configuration, which is then pre-stretched to a lower profile using an actuator which is a rigid rod; the occluder is then mounted onto the delivery catheter device. A release mechanism in the delivery device removes the stretching force applied to the rigid rod, and thereby causes the occluder to revert to its pre-set bulbous configuration, thereby occluding the body lumen. The delivery catheter is threaded into the appropriate location either through a sheath or through a hysteroscope and by using an appropriate mechanism, the two end structures of the occluder are brought together and the occluder is delivered into the body lumen causing immediate occlusion of the lumen.

In either case using an appropriate mechanism, the two end structures of the frame are brought together resulting in an expanded bulbous structure, causing immediate occlusion of the lumen.

The small narrow rounded frame is made from a metallic or polymeric tube by cutting, molding or machining appropriate longitudinal slots, or openings, on its surface, so that expanding of the slotted tube using any means to bring its' end structures towards each other as previously described, yields in a structure that is several times larger than its original diameter and continues to remain at its final expanded diameter depending on the to the degree to which the two end structures are brought towards each other. The pulling mechanism or the actuator in one case is a thread, made form high strength plastic, textile, or metal that contains a "knot" or ratchet which when is pulled through a constriction or lock located at the proximal end structure of the occluder prevents the deformation so produced in the rounded frame to form the enlarged bulbous nature from returning to its original low profile shape. In the other instance, the rigid rod maintains the frame in its low profile form during delivery and release of which causes the frame to revert to its preset bulbous configuration.

Additionally the material of the frame is made to undergo deformation beyond its yield point and therefore will remain at or near its expanded larger profile bulbous condition. The initial diameter of the slotted tube is substantially small (less than 1 mm) so that the initial profile of the rounded frame and the entire device is small enough to thread through a delivery catheter or a hysteroscope depending on the purpose of its use. The slots or openings on the surface of the rounded frame can be lengthwise, spiral or at an angle to its longitudinal axis providing four to six longitudinal members. The longitudinal members are made such that there is a slight convexity or bulge radially outwards promoting an outwardly deformation when the two end structures are brought together. The number of slots around its diameter also depends on the surface available on the frame for providing sufficient slots, with a typical design consisting of four to six slots. The slots can be arranged in many different configurations having the general sinusoidal or triangular undulations or any other shape that would make the slotted tube flexible. The width and the length of the slots/longitudinal members are determined by the initial diameter, hence the surface area, of the rounded frame and the ratio of the expanded and the non expanded diameter of the frame.

The occluder is mounted on a delivery catheter flexible enough to go through a guiding catheter, sheath or other devices such as a hysteroscope. The delivery device which is equipped with a pull member enables it to pull the two end structures of the frame towards each other controllably such that by manipulating a mechanical means in the delivery device handle, the operator will be able to deform the rounded frame controllably. As such a dial or similar means can be provided in the delivery catheter handle for the operator to preset the extent to which the frame is expanded.

The occluder is encased in a bio-compatible expandable material, such as silicone, polyurethane or any other soft, expandable polymeric or biological material that can be used to encase or surround the occluder and its distal end partially or completely. The encasing material can be loosely mounted on the occluder or can be well bonded to the metallic or polymeric longitudinal members of the frame of the occluder but shall not separate or come loose from the longitudinal members during expansion and during deployment.

The occluder is provided with an additional structure proximal to it, the anchor, which is attached to the frame or is made a part of the frame to form the complete device. This anchor is typically 30-40 mm long and has between 4-8 thin long elements or "axial rods" made either from molded plastic or from metals. These long axial rods are connected circumferentially with additional circumferential connecting members that have a curved shape. The thin long axial rod elements and the circumferential curved connecting members form the anchor which provides additional anchoring means for the occluder. While the anchor means provides additional anchoring of the occluder, the occluder can be made without the anchor, which may be suitable for certain applications. The occluder is placed in the lumen to be occluded either completely within the lumen or in such manner that a portion of the anchoring means is outside the lumen to be occluded. This structure formed as described above, i.e. the anchoring means, is a thin generally hollow, tapered or non-tapered structure, with longitudinal axial rods and circumferential connecting members folds-in easily when the occluder is threaded through the delivery lumen of a delivery catheter or such delivery device as a hysteroscope. Once delivered, the flexible, thin hollow anchoring means generally expands due to its shape memory elastic properties and abuts the inner wall of the lumen to be occluded.

Additionally the actuator pull member can be provided with more than one knot or ratchet, so that the frame can be ratcheted to expand to different bulbous diameters. This feature allows the frame to be expanded to a diameter even larger than the lumen to be occluded so as to physically lock the frame in the lumen's tissue and will prevent the migration of the occluder device within the occluding lumen.

The occluder generally has several longitudinal members. These longitudinal members can have specific shapes that will give the expanded bulbous occluder specific shapes. For example longitudinal member with a uniform width would provide a shape similar to an oblong body like a sausage when expanded. Longitudinal member where the width uniformly decreases from each end to the center will yield an oblong shape when expanded. As such depending on the application, as to the type of body lumen to be occluded, the longitudinal members can be designed to satisfy the actual need for the application. The preferred embodiment will be a hollow thin tube consisting of four to six longitudinal members, and therefore four to six longitudinal slots, that are about 10 mm long ending in a closed hemispherical cap. An actuator pull thread mounted into the inside of the cap consisting a knot or ratchet in about the middle runs within the rounded frame passes through a restrictor or a lock at the proximal end structure of the frame. This frame assembly is attached by suitable means to a hollow anchoring means which consists of a structure containing four to six thin axial rods, which are connected circumferentially by additional circumferential members which forms a thing, flexible, hollow, tapered polymeric or metallic structure which can squeeze to a smaller profile, yet expand to its predetermined size when deployed into the body cavity. The distal portion of entire occluder, especially the rounded frame is covered by a thin impervious membrane, which is expandable and remains on the outside of the occluder frame after the occluder is delivered into the body cavity.

Once the occluder consisting of the afore mentioned impervious membrane is delivered into the body lumen, the body lumen is totally occluded and no blood, body fluids or semen will pass through the lumen.

Alternatively the actuator pull member can be made of an elastomeric thread or a thread containing an elastomeric material reliably attached to it. When the actuator is pulled through the restrictor or the lock, the elastomeric nature of the actuator, which would deform during tensioning reducing its profile so as to get through the lock, yet on expansion will lock the actuator at any desirable state as the pull member is pulled through the restrictor. The said actuator may also contain knots or ratchets at various points to provide a step by step locking or ratcheting feature.

The encasing materials, such as silicone usually have elastic properties. As such when the rounded frame is expanded, there is some degree of recoil (back) of the frame, which may cause an improper hermetic seal. Therefore the frame can be designed to have a larger diameter than the lumen to be occluded. This is accomplished by providing several separate knots in the actuator with each knot defining a specific diameter of the frame when the two ends of the frame are brought towards each other.

Alternatively the frame can be pre-shaped to the desired diameter. This can be achieved by using shape memory alloys such as nickel titanium alloys or can be molded in polymeric materials such as nylon, polypropylene, polyethylene, polyurethane or in any suitable biocompatible material to a predetermined shape and size. Such a frame can be elongated using a push mechanism, by a rigid push rod, to reduce its profile to a suitable size for the intended application and the push mechanism is withdrawn after the deployment of the occluder, returning the occluder back into its predetermined shape and size. The above embodiment shall also contain an impervious sheath such as a silicone sheath either over, or encasing the slotted tube. Such an embodiment shall be the same in function as the previous embodiment described herein, in which the shape and size are changed at will by using a pull member actuator, and the final structure, form and function of the two forms are essentially identical while the method of deployment is different.

The above described device is an occlusion device to occlude a body lumen, which is made from a slotted tube frame encased with an expanding, yet impervious membrane, which is deployed by mechanical activation to transfer it from its original thin low profile form, to a larger bulbous shape having a diameter much larger than the lumen to be occluded. Upon delivery the occluding device anchors in the lumen and provides a complete occluding "wall", closing the lumen and preventing the flow of fluids or matter across the occluder. As such, this device and various modification of it, and various modified methods of delivery will provide permanent occlusion of a body lumen when properly implanted in a body lumen. The advantage of the present invention is that immediate hermetic seal and a complete occlusion of the lumen are achieved by the proper placement of the occluder. This device additionally does not depend on tissue growth or tissue scaring to occlude the lumen as is the current practice in occluding body lumens, which not only takes nearly two to six months but in some instances not very reliable. The proposed invention and the method thereof do not require additional medical procedures or tests in a few weeks or months after the procedure to check or verify that the lumen is occluded or the efficacy of occlusion.

BRIEF DESCRIPTION OF THE DRAWINGS

FIG. 5(*a*) shows a specific design for the slotted tube which on deployment acquires a long tubular shape structure.

FIG. 5(*b*) shows a specific design for the slotted tube which on deployment acquires an oblong shape structure.

FIG. 5(*c*) shows a specific design for the slotted tube which on deployment acquires a disk shape structure.

DETAILED DESCRIPTION OF THE PREFERRED EMBODIMENT

Figure 1:
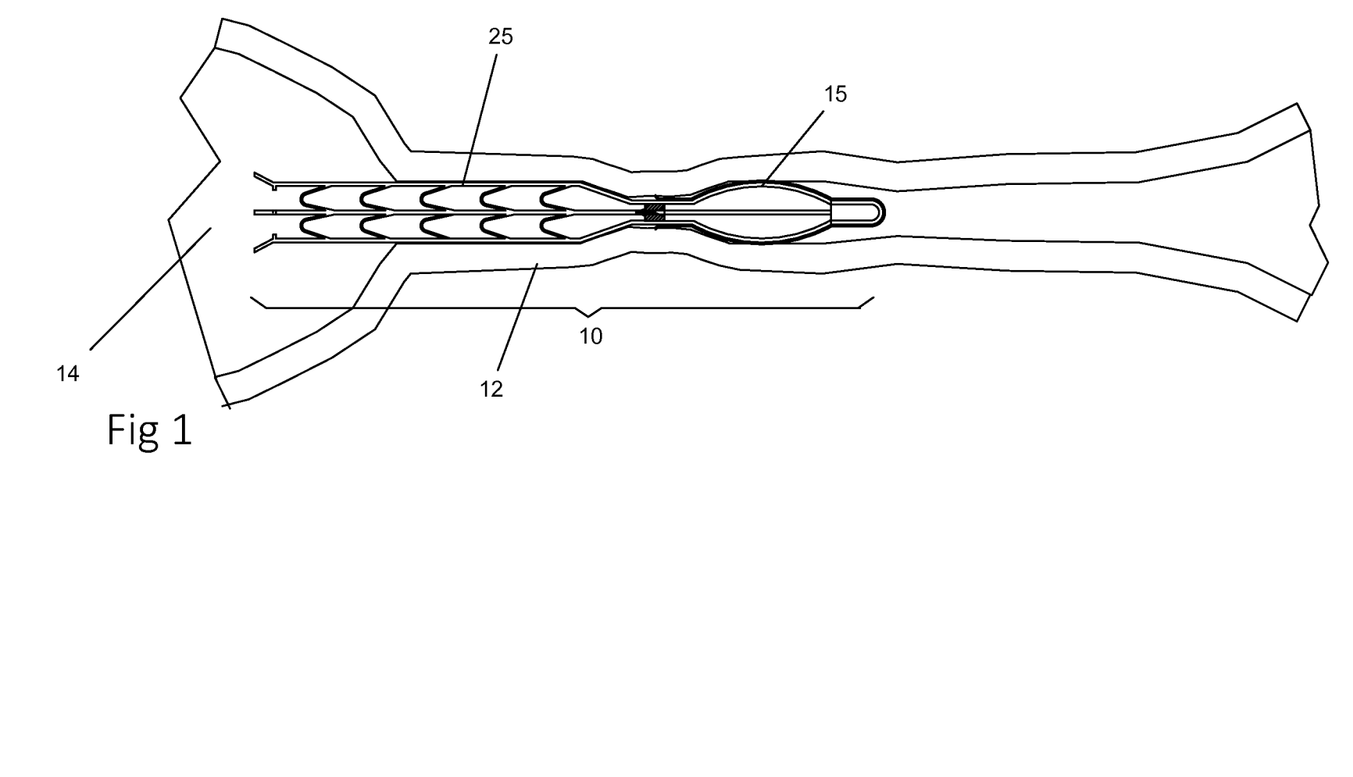
FIG. 1 shows the preferred embodiment when it is deployed in one-type of body lumen, namely the fallopian tube.

FIG. 1 shows the lumen occluding device (10), consisting a narrow cylindrical rounded frame structure (15) to which a anchor section (25) is attached proximally, after the entire device has been deployed into a fallopian tube (12). The fallopian tube (14) is a very narrow tubular lumen through which an egg, or ovum, enters the uterus. The device can be implanted such that a portion of the anchor portion is within the uterus as shown in FIG. 1.

Figure 2:
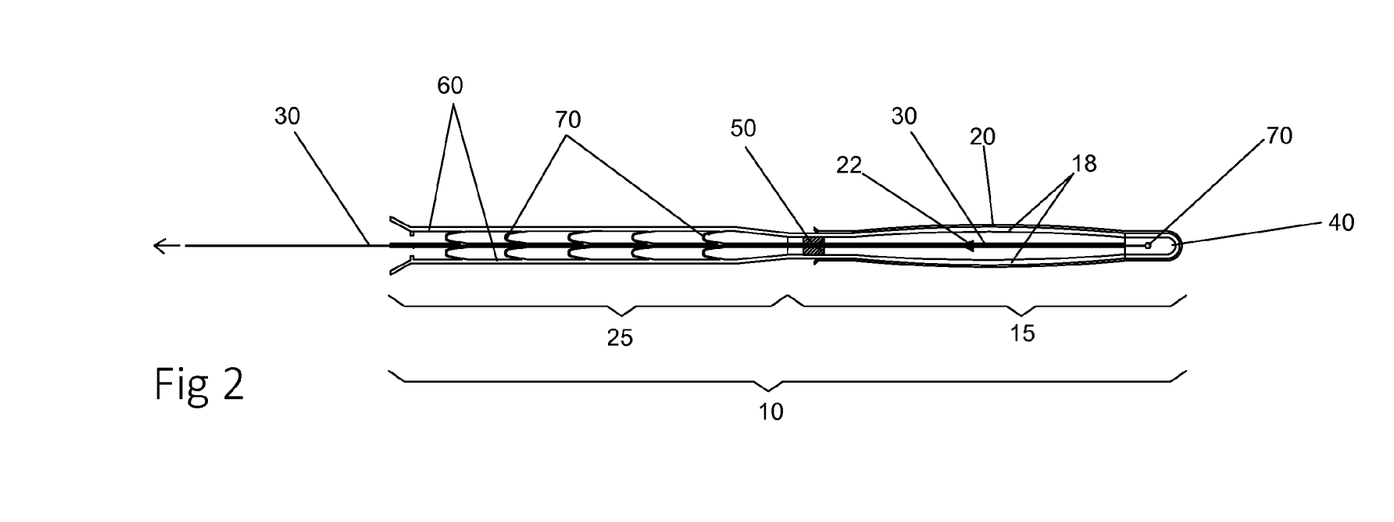
FIG. 2 shows the preferred embodiment in its pre-delivery configuration, the desired configuration prior to, and during, deployment into a body lumen.

The FIG. 2 describes the device (10) consists of two main components; a low profile rounded frame in the form of a slotted tubular section (15) and an impermeable expandable sheath (20) encasing the slotted tube frame. The slotted tube consists of four to six longitudinal members (18) forming four to six slots, which have a general bulged and convex configuration these in turn facilitates the deformation of the frame radially outwards without kinking when the occluder is deployed. The frame (15) ends distally in an end structure which is a closed and is hemispherical having a smooth cap (40). The thin tubular frame (15) is covered or encased at least partially by the impervious silicone sheath (20). An actuator pull string (30) is attached securely to the distal end structure and within its distal cap (40) as shown at location (70). The actuator pull string (30) threads through the rounded frame (15) and passes through the proximal end structure containing the lock (50). The pull string is provided with a knot or ratchet (22) feature mounted at a location between the two end structures of the slotted tube frame. By pulling the pull string (30) while holding the proximal end structure of the frame is at rest causes the frame to bulge out and become bulbous and therefore increases its diameter and profile as shown in FIG. 3. The degree to which the slotted tube bulges out depends on to the degree to which the actuator pull string (30) is pulled. The proximal end structure of the frame contains a lock mechanism (50) which has a hole slightly smaller than the knot (22) such that when the knot passes through the lock (50), the lock prevents the thread from retracting, and actuator pull thread remains in place without recoiling back, thereby holding the rounded frame in its new deformed bulbous form. The silicone sheath (20) deforms along with the frame and acts as a wall or barrier to the passage of any fluids or matter across the occluder when implanted in the body lumen.

The rounded frame (15) is connected to an anchor portion (25) at its proximal end or is made as part of the occluder (10). The anchor provides additional stability to the occluder (10) by providing increased surface area for anchoring. The anchor portion (25) consists of four to six thin long longitudinal axial rod elements (60) generally placed in a hollow cylindrical configuration. These thin longitudinal axial rod elements (60) are circumferentially connected at regular intervals with circumferential connecting members (70) forming a cage type structure. The circumferential connecting members (70) have a curved configuration which facilitates the folding and collapsing of the anchor (25) to a low profile when it is passed through the lumen of a delivery catheter or a hysteroscope.

FIG. 3 describes the deployed configuration of the occluder. The ratchet (22) has passed through the lock (50) and holds the deformed bulbous shape of the rounded frame (15) in its deployed dimension. The anchor portion (25) is made thin and flexible but with some degree of memory so that it will expand to its pre-set size and shape on placement and expansion. Various modifications of the ratchet and the lock can be designed in order to accomplish the same outcome. The entire device is designed to result in a low profile configuration depending on the application. In most applications the initial profile of the device will be around 1 mm and the deployed dimension shall be between 2-6 mm.

FIG. 4 describes an alternate mechanical means to change the shape of the rounded frame from its original low profile to its pre-set predetermined deployed state. In this case instead of a pull string actuator as previously described, a rigid push rod actuator (32) is used to maintain the initial thin low profile of the rounded frame occluder. A knot or ratchet (22) similar to the previous embodiment is provided on the rigid push rod actuator to hold the frame stretched and elongated. The lock (52) which now acts in reverse holds the knot (22) in place which in turn holds the rounded frame in its stretched low profile and elongated configuration.

Figure 5:
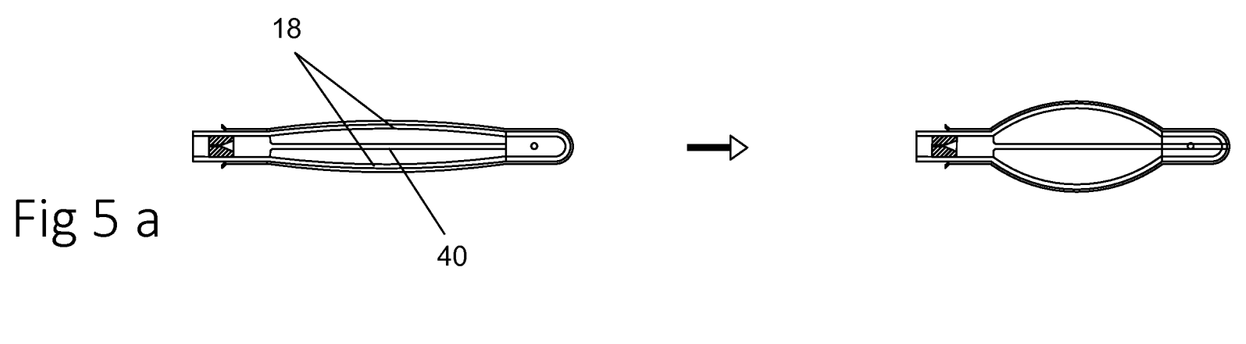

FIG. 5(a)-(c) shows variations of the longitudinal members (18) which will define and facilitate, as to, how the rounded frame or structure will deform when actuated by mechanical means as described before. The uniform longitudinal member in FIG. 5(a) will deform the structure on mechanical actuation to form an elongated shape such as a "hot dog" and while the structure in FIG. 5(b) with longitudinal member (24) having a smaller dimension at the center than at its ends, will deform on mechanical actuation to form more of an "oblong" shape, whereas the structure in FIG. 5(c) with longitudinal member (26) having a notch at the center will deform the frame more to a form of a "disk". In either case the expanded diameter will be larger than the initial diameter and can be designed accordingly the size of the lumen that will be occluded by the occluder (10).

Figure 6:
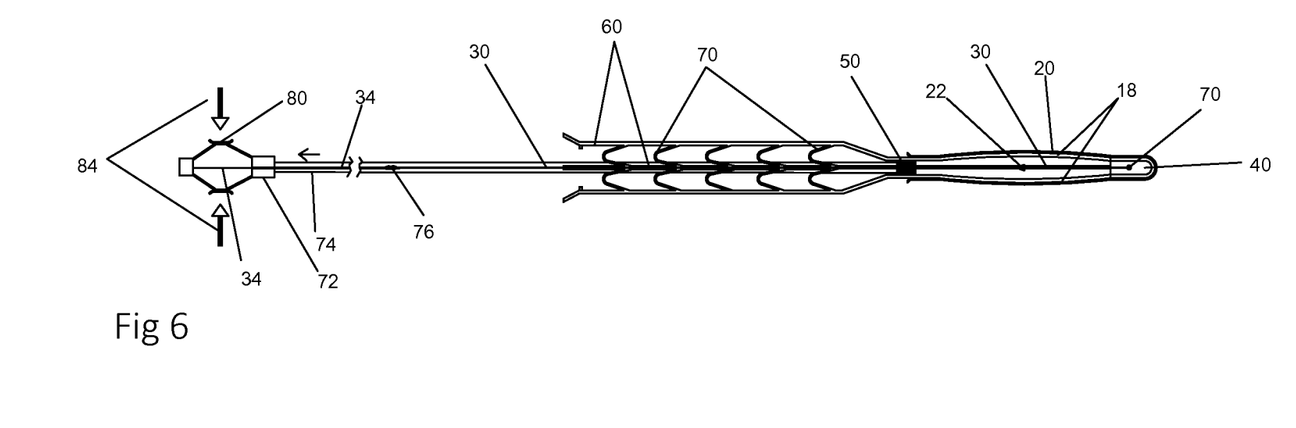
FIG. 6 shows the preferred embodiment of the device when it is attached to its delivery device which is used to place and deploy the device in a desired body lumen.

FIG. 6 describes a flexible delivery catheter (72) capable of tensioning, delivering, deploying and releasing the occluder (10) into an appropriate body lumen. The deliver catheter specifics will depend on the type and location of the body lumen to which the occluder (10) will be delivered. In general the delivery catheter consists of a flexible, torqueable shaft (74), preferably made from a braided plastic tube or from plastic encased wire coil, having a proximal delivery trigger mechanism (80). The rounded frame (15) is deployed either by pulling on a pull thread actuator (30) or pulling on the push rod actuator (32) of the tensioning device (72). In a typical configuration elongated member consisting of a pull string (34) of the delivery catheter/tensioning device is looped around the end loop of pull string (30) of the occluder at the location (76). Triggering to deploy the occluder by squeezing the releasing buttons (80) as shown by arrows (84) would be one possible manner to deploy the occluder in to the body lumen. After the delivery, the elongated member (34) is cut off and the delivery catheter is removed leaving the occluder (10) in the lumen which is occluded, after which the pull string (34) of the elongated member is carefully removed from the body by pulling on one end of the pull string (34).

Similar mechanism can be used to release the occluder (10) from the delivery catheter when the slotted tube (15) is delivered in the pre-stretched configuration.

I claim:

1. An occluding device for lumen that otherwise allows fluid flow, comprising:
    an elongated tubular rounded frame comprising at least one generally longitudinal slot;
    an elastomeric sheath surrounding said tubular rounded frame so that when said frame is actuated to enlarge in a lumen said sheath moves into contact over the substantial length of said sheath with a surrounding wall that defines the lumen to immediately stop flow said lumen;
    an anchor located proximally of said frame and axially spaced from said frame further comprising a plurality of axially oriented members connected to each other circumferentially with curved and spaced flexible elongated connecting members in the shape of rings, said anchor presenting openings between said axially oriented members and said connecting rings, said anchor, when disposed at least in part in said lumen with said frame, preventing axial movement of said frame in said lumen in opposed directions;
    an actuator extending within said frame for remote mechanical actuation of said frame for occluding said lumen;
    said actuator is unlocked to said frame for lumen placement and selectively locked to said frame after radially extending said frame.

2. The device of claim 1, wherein:
    said actuator is loaded in tension to radially extend said frame and said surrounding sheath.

3. The device of claim 1, wherein:
    said actuator is loaded in compression to radially extend said frame and said surrounding sheath.

4. The device of claim 1, wherein:
said actuator comprises a rigid rod.

5. The device of claim 1, wherein:
said actuator comprises a string.

6. The device of claim 1, wherein:
said frame has a closed distal end.

7. The device of claim 1, wherein:
said frame is introduced with a catheter with said actuator extending through said catheter.

8. The device of claim 7, wherein:
said actuator comprises a flexible elongated member extending from a distal end of said frame, said flexible elongated member further comprising a distal portion forming a proximal end loop and a proximal portion threaded through said loop and extending outside a proximal end of said catheter.

9. The device of claim 8, wherein:
the proximal end of said proximal portion of said elongated member is secured to a tensioning device supported by said catheter.

10. The device of claim 9, wherein:
said catheter is removable after said proximal portion of said elongated member is released from said tensioning device, said proximal portion of said elongated member is then removable with a force on one of its two ends to remove the opposed end through passage through said proximal end loop.

11. The device of claim 1, further comprising:
said actuator extending through said anchor, said anchor engaging the wall of the lumen over the substantial length of said anchor.

12. The device of claim 11, wherein:
said connecting members comprise a plurality of bends.

13. The device of claim 1, wherein:
said frame further comprises a plurality of spaced longitudinal members connected to opposed end structures, said longitudinal members flexing as a result of relative movement of said end structures.

14. The device of claim 13, wherein:
said longitudinal members flex outwardly when put into compression by said relative movement of said end structures caused by said actuator.

15. The device of claim 13, wherein:
said longitudinal members flex outwardly when put into tension by said relative movement of said end structures caused by said actuator.

16. The device of claim 13, wherein:
said longitudinal members are at least one of uniform along their length, non-uniform along their length and notched along their length.

17. The device of claim 1, wherein:
at least a portion of said actuator is releasable from said frame after said frame flexes radially.

18. A lumen occluding device, comprising:
an elongated rounded anchor frame comprising a plurality of axial rods held in a tubularly shaped spaced relation by a plurality of axially spaced, flexible, circumferentially extending while curved elongated connecting members, said connecting members moving radially for occluding the lumen;

a sheath surrounding an elongated tubular rounded frame comprising at least one generally longitudinal slot and disposed distally of said anchor frame, said rods and connecting members of said anchor frame anchoring said elongated tubular rounded frame for closing off a passage therethrough, said elongated tubular rounded frame actuated by an actuator extending through said anchor frame and said elongated tubular rounded frame for actuating said elongated tubular rounded frame to enlarge, said sheath enlarging in the lumen with said elongated tubular rounded frame until said sheath is in contact over the substantial length of said sheath with a surrounding wall that defines the lumen to immediately occlude said lumen and to prevent axial movement of said elongated tubular rounded frame in said lumen in opposed directions, said anchor frame enlarging in the lumen independently of said elongated tubular rounded frame with a release of stored potential energy stored therein to secure the position of said elongated tubular rounded frame and said sheath that surrounds said elongated tubular rounded frame to the lumen.

19. The device of claim 18, wherein:
said connecting members comprise a plurality of bends.

20. The device of claim 19, wherein:
said connecting members allow said tubular shape to compress to enter the lumen and expand on placement therein.

* * * * *